US00PP13930P29

(12) United States Plant Patent
Cox

(10) Patent No.: US PP13,930 P2
(45) Date of Patent: Jul. 1, 2003

(54) APPLE TREE CALLED 'STELLA MINNESOTA'

(76) Inventor: William A. Cox, Rte. 1, Box 216, Cleveland, MN (US) 56017

( * ) Notice: Subject to any disclaimer, the term of this patent is extended or adjusted under 35 U.S.C. 154(b) by 0 days.

(21) Appl. No.: 09/631,500

(22) Filed: Aug. 3, 2000

(51) Int. Cl.[7] ..... A01H 5/00
(52) U.S. Cl. ..... Plt./161
(58) Field of Search ..... Plt./161

(56) References Cited

U.S. PATENT DOCUMENTS

PP4,824 P 2/1982 Lautz ..... Plt./34
PP11,367 P 4/2000 Luby et al. ..... Plt./161

*Primary Examiner*—Bruce R. Campell
*Assistant Examiner*—Anne Marie Grünberg
(74) *Attorney, Agent, or Firm*—Merchant & Gould P.C.

(57) ABSTRACT

A new and distinct variety of apple, fruit and tree called "Stella Minnesota" provides a fruit having improved taste and crispness, resistance to browning, characteristic white star marks in the fruit skin and in the tree, shows large green leaves.

7 Drawing Sheets

FIELD OF THE INVENTION

The invention relates to a new and distinct variety of an apple fruit and apple tree (*Malus domesticus*) called "Stella Minnesota". Growers, marketers, and consumers are continually looking for new apple species to provide heretofore unavailable qualities. Among desirable qualities are eating qualities such as crispness, sweetness, flavor and skin texture. Utility in salads, cooking, sauces and other apple products benefits from early development and taste and color stability. A need has existed for some time for apples that resisted browning, once cut, apples that have excellent eating qualities, early ripening and other desirable properties.

BACKGROUND OF THE INVENTION

The *Malus domesticus* apple variety of the invention is an early season apple, excellent for fresh eating, salads, sliced applies, dried apples, sauce, pie and desserts. The claimed plant is a chance seedling discovered growing from composted apple pomace in the garden at Cox Apple Orchard near Cleveland, Minn. Parentage of claimed plant is unknown, whereas seeds could have sprouted from any one of twenty-five named varieties, or three unnamed seedlings in the orchard. The variety has been grafted to known root stock.

Some characteristics of the claimed plant are somewhat similar to well known named cultivars such as Cortland, Paulared, Famuse (Snow Apple), State Fair, and Haralson, but similarities only match one or two characteristics with differences in at least three traits of each of the above-named cultivars.

There is resemblance to Cortland in two respects, as both have some fruit set on terminals. The white flesh of the fruit is somewhat similar, but the flavor and texture are different. Other obvious differences are the leaf shape and size, the growth habit of the tree, and the coloration of the fruit.

The resemblance to Paulared is the season of maturity of the fruit. The differences are in the growth habit of the tree. The leaf pattern of Paulared clusters more with more blind wood between clusters and fruiting spurs. The leaf shape of Paulared is more enlongated and typically smaller. The color of mature Paulared fruit is a different shade of red versus red-orange. The flavor and texture of the fruit is different in that the Paulared fruit is generally milder, softer, less crisp and breaking, with having less shelf life.

Similar to Famuse is the strikingly white flesh of the fruit and a hint of the same flavor. The differences are in coloration of the fruit exterior, the season of maturity, tree growth habit, and leaf structure.

There is a resemblance of the claimed plant to the Haralson cultivar in that the bare wood in dormant season has a reddish caste particularly on two to four year old wood. The texture of the fruit is similar in crispness, but the flavor of the Haralson is much more tart versus sweet, and Haralson's season of maturity is later in the fall. Haralson fruit (some strains) has white dots upon a red coloration, but the claimed plant's fruit has fewer but larger star-shaped white dots upon a red-orange color. The two differ also in tree growth habit and leaf shape.

The resemblance to State Fair is also limited to two traits; the season of maturity and the extraordinary amount of leaf surface due to large leaf size and abundance. The most obvious differences include leaf shape and coloration, the tree form and growth habit, and the color and flavor of the fruit. State Fair parentage of the claimed plant is unlikely because there were no State Fair trees in the orchard previous to growth of the seedling.

SUMMARY OF THE INVENTION

The present invention relates to a new and distinct variety of apple, fruit and tree, called "Stella Minnesota". This tree provides a fruit having improved taste and crispness, resistance to browning, characteristic white star marks in the fruit skin. The fruit ripens early in the season, has long storage life, excellent flavor, crisp, juicy texture, and a utility in common apple products. The tree shows large green leaves and combines the characteristics of having a compact form with vigorous growth, angled branches, and annual fruit production.

BRIEF DESCRIPTION OF THE PHOTOGRAPHS

The drawing and photographs show novel characteristics of white stars over red-orange color, yellow under color progressing to overall color.

Note the stem cavity is still green even on fully ripened fruit. Apple photographs show medium stem length, shorter than some, longer than MacIntosh. Tree photographs show claimed seedling tree with multiple wide angled branches. Leaf photographs show larger size and shape of leaf from claimed plant. Smaller more elongated leaf of Red Delicious are markedly different. Nursery photograph shows vigor of young propagules in the first month of their first leaf. We have noted that the graft plant on a Bud 9 rootstock was insect and disease resistant without addition of spray insecticides and treatments. We have also found that the variety grown on Honey crisp trees show resistance to fire blight spread.

FIG. 2 shows four individual fruit products of the variety of the invention showing the red-orange color with yellow undercolor at the stem. The fruit also shows areas of yellow in the fruit skin overall.

FIG. 3 shows a tree of the variety with fruit ripening on the tree showing coloration placement, shape, leaf size, branching and other variety characteristics.

FIG. 4 shows fruit of the variety growing and ripening on the tree. The figure shows fruit, leaves, branching and other characteristics and shows the character of the leaves on the tree in the foreground.

FIG. 5 shows the tree of the variety-budded onto bud 9 rootstock grown in an experimental plot.

FIGS. 6 and 7 show the leaf of the variety. The leaves have marked larger size than conventional leaves such as red delicious and are unique in coloring and shape.

DETAILED DESCRIPTION OF THE NEW VARIETY

Figure 1:
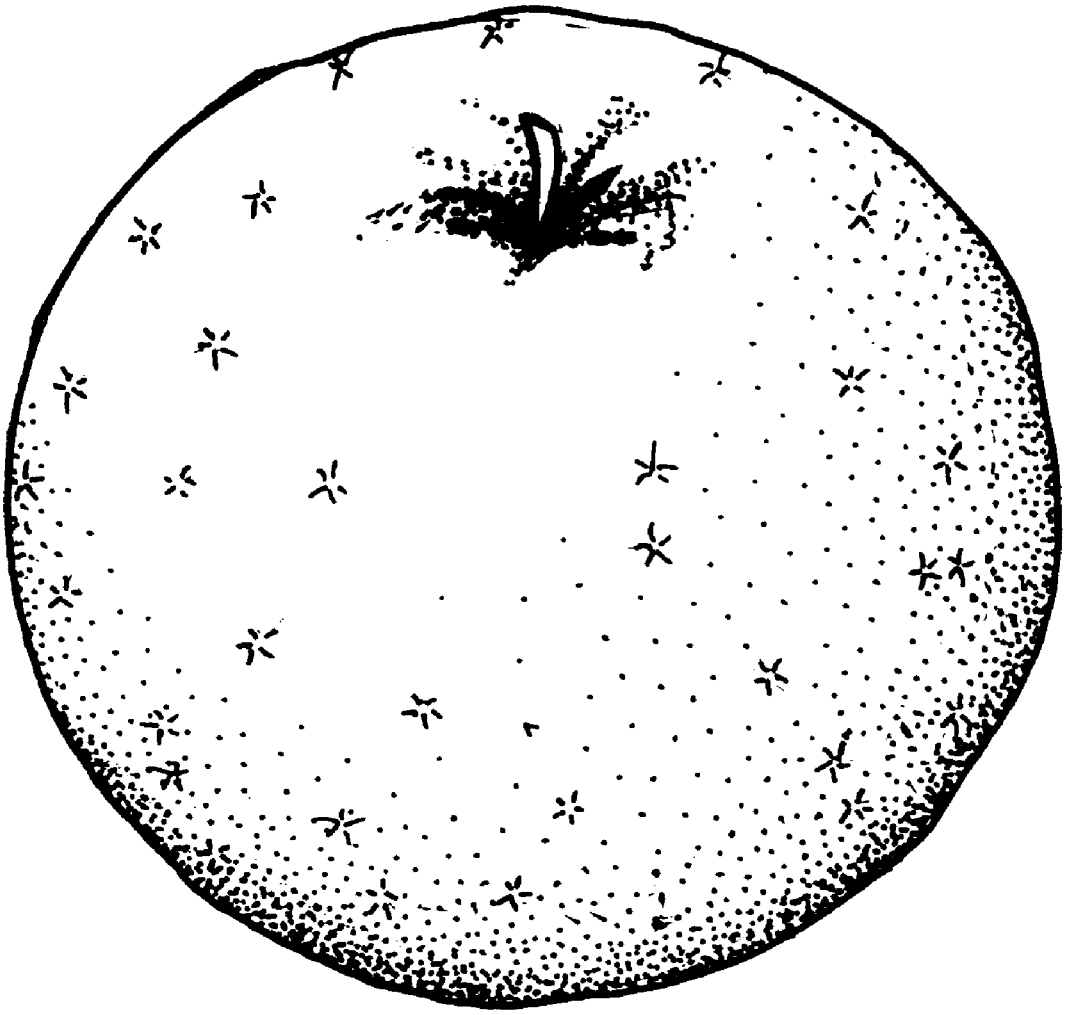
FIG. 1 shows a drawing of the star marked skin of the fruit of the tree of the variety.

Propagules of the claimed plant have been propagated under contract with Shefflebine Nursery at West Salem, Wis. The claimed variety advantageously grows on its own seedling rootstock or on Budagonsky 9 (Bud 9) rootstock. Propagules budded and grafted onto three different rootstocks (Mark, MM26, and Malling 7A) all show identical characteristics of the claimed plant.

The unique qualities of the apple include moderately vigorous growth with many wide angled (nearly horizontal) branches and a compact growth habit with spurs at short to medium intervals. The tree leaves tend to be larger than common varieties by at least 10% or more. At 30 cm height and 12 years of age the trunk has a diameter of 10.5 cm. The trunk bark texture can be described as smooth. The mature tree has branches 2 m long and 4.3 cm diameter at the trunk. The branches are nearly horizontal. The branch bark texture can be described as smooth with slightly raised lenticils. The lenticils have an average size of 0.6 cm, can be described as slightly raised from the bark, and number 5 per 1 square centimeter. Lenticil color is 156D, according to The R.H.S. Colour Chart.

The fruit has a unique star-like surface character that forms white (157C to 155B according to The R.H.S. Colour Chart) star-like features in the red-orange (42A according to The R.H.S. Colour Chart) color of the apple. The star-like forms appear throughout the apple, but often are prominent at the top of the fruit. The flesh is remarkably white (155B according to The R.H.S. Colour Chart), dense, crisp and juicy with a small seed core. One important characteristic is that the apple flesh does not oxidize (turn brown) and remains white for at least a day or more after slicing.

The claimed plant is moderately vigorous with many wide-angled branches and is quite compact in growth habit with spurs at short to medium intervals. The bark has a reddish cast on second through fourth year wood (166C according to The R.H.S. Colour Chart). The claimed plant has been precocious and annually productive. That is, the claimed variety bears fruit annually. The fruit tends to cluster with some fruit set on terminal buds. The leaves are large and wide at the stem end.

The flowers are large and bloom in unison with MacIntosh. The variety is self fertile, which has been tested by allowing a natural pollination without bringing in hives of honey bees. The flowers are scented with a scent that can be described as mild and typical apple blossom aroma. The time of bloom is typically about May 9.

The fruit of the claimed plant is large, round, moderately oblate, the stem is medium length, the stem cavity stays green in color (152C to 152A to 141C according to The R.H.S. Colour Chart), and calyx basin is shallow.

The season of harvest begins in late August to early September in south central Minnesota and fruit retains firmness for several weeks in cold storage. The date of last picking for the claimed apple tree is between September 15 and September 20.

Fruit color starts with a red-orange blush progressing to a full brilliant red-orange (42A according to The R.H.S. Colour Chart) with multiple white stars (157C to 155B according to The R.H.S. Colour Chart) dispersed overall. The color patterns on the fruit can be described as yellow ground color (157C to 155B according to The R.H.S. Colour Chart), red orange overstriping (42A according to the R.H.S. Colour Chart), progressing to 60% to 90% red orange overcolor (42A according to The R.H.S. Colour Chart)and the red orange overcolor (42A according to The R.H.S. Colour Chart) covers 75% of the fruit at harvest. The flesh is remarkably white (155B according to The R.H.S. Colour Chart), moderately dense, very crisp and juicy and the seed core is small.

The flavor of the fruit from the claimed plant has been described as a great balance of sweet and tart, sparkling and excellent, with fall apple quality in summer apple season. The flavor and aroma remain pleasantly consistent through two months in storage. The flesh does not oxidize (turn brown). The flesh of the fresh fruit remains white (155B according to The R.H.S. Colour Chart) for days and, upon drying, remains white even weeks after slicing.

The claimed plant is cold tolerant, winter temperatures of far below 0° F. have not caused any sign of freeze injury to twigs, branches or trunk. Claimed plant is slightly susceptible to scab. The claimed plant shows no obvious substantial susceptibility to powdery mildew or fire blight. No damage from aphids or mites has been observed and no visible foliar damage from leaf hoppers has been apparent, in contrast to the Honey Crisp variety grown nearby. The claimed plant responds to thinning compounds much more so than the Haralson or Paulared cultivars, possibly due to the extraordinary quantity of leaf surface.

Originally, Applicant employed his own experience with colors for stating the colors of the various parts of the fruit and tree. Subsequently, Applicant has confirmed these color assignments employing The Royal Horticultural Society (R.H.S.) Colour Chart. The colors, according to The R.H.S. Colour Chart, of certain portions of the claimed apple tree, flower, or fruit are described in the following table:

| Part of Tree | Representative Color From RHS Colour Chart |
|---|---|
| Petiole | N134C |
| Locule | 155A |
| Seed, Immature | 157D |
| Seed, Mature | 166A |
| Trunk Bark | 156A |
| Branch Bark | 165A |
| Reddish cast of bark on 2nd and 4th year wood | 166C |
| Flesh | 155B |
| Lenticil on bark | 156D |
| on apple | 157C |
| Stem | 152C |
| Stem Cavity | 152C to 152A to 141C |
| Pedicel | 135B |
| Bud (Balloon Stage) | N57B |
| Petal (Upper Surface) | 62D to 69D |
| Petal (Lower Surface) | 62D with tinges of N66B |
| Stamen | 155C |
| Flower | N155B |
| Upper Surface of Immature Leaves | 144C |
| Lower Surface of Mature Leaves | N138B to 134A |
| Upper Surface of Mature Leaves | 141C |
| Lower Surface of Immature Leaves | 135B to 135C |
| White Stars of Fruit | 157C to 155B |
| Fruit Undercolor | 157C to 155B |
| Fruit Blush | 42A |

Measured sizes of various portions of the claimed apple tree, flower, and fruit are described in the following table:

| Part of Tree | Size (cm) |
|---|---|
| Leaf Width | 5.5 cm |
| Leaf Length | 9 cm |
| Fruit Size | 8.2 cm (diameter)<br>6.5 cm (height) |
| Fruit Axial Cross Sectional Diameter | 6.5 cm |
| Fruit Transverse Cross Sectional Diameter | 8.2 cm |
| Fruit Weight (grams) | 95 g (7 cm fruit),<br>149 g (7.6 cm fruit) |
| Petiole (Leaf Stalk) | 2.3 cm |
| White Stars on Fruit | 0.2–0.5 cm |
| Pedicel (Flower Stalk) | 1.3 cm |
| Seed Core | 1.5 cm × 2 cm |
| Bud | .2 cm (dormant)<br>.6 cm (spring before bud break) |
| Stamen | 0.6 cm<br>thirteen per flower |
| Pistil | 0.4 cm<br>each flower has one at the base which divides into four |
| Petal | 1.7 cm (length) ×<br>1.3 cm (width) |
| Flower | 3.1 cm |
| Fruit Stem | 2 cm > .2 cm width |
| Petiole | 0.8 cm |
| Locules | 1.5 cm ×.9 cm width |
| Stem Cavity | 3 cm × 2.2 cm deep |
| Calyx Basin Depth | .6 cm |
| Calyx Basin Width | 2.5 cm |

The following traits have been repeatedly observed and measured and include those characteristics that distinguish this apple tree as a new and distinct cultivar.

Tree

The new variety is characterized by a tree form that is spreading with moderate to vigorous growth. The vigor is inherently directed during the first few years of growth into multiple lateral branches with short internodes that attains a spur-type growth habit. The height of the original 12 year-old tree is approximately 16 feet and the width is approximately 12 feet wide. There has been no obvious winter injury to trunk, branches, twigs, or buds on this variety at the location at Cleveland, Minn. It has proven to be slightly susceptible to apple scab and cedar apple rust and slightly resistant to fireblight. Dormant one-year-old shoots are lightly pubescent, the color of the shoots are brown (165A according to The R.H.S. Colour Chart). Two-year-old wood, three-year-old wood, and occasionally four-year-old wood has a slightly redder caste, especially on the sunny side (166C according to The R.H.S. Colour Chart). On one-year-old shoots internodes are 0.7 cm to 1 cm measuring the middle part of the shoot. Lenticels are medium in number and size. The lateral buds are adpressed, medium in size and bud support is medium.

Leaves

The leaves are lightly pubescent on a growing young shoot tip. Shoot tip leaves are usually concave. The upper side of immature leaves are a yellow green, 141 C according to The R.H.S. Colour Chart. The lower surface of the immature leaves are a green, 135B to 135C according to The R.H.S. Colour Chart. The upper surfaces of mature leaves are yellow-green, 141 C according to The R.H.S. Colour Chart. The lower surfaces. of mature leaves are green, N138B to 134A according to The R.H.S. Colour Chart. The leaves are entire and not lobed, have an outward orientation from the stem, small stipules, mucronate apex, and a crenate indentation of the margins that is barely discernable. Glossiness on the upper side is faint. The leaves have no anthocyanin discoloration under normal growing conditions. For fully expanded leaves the mean petiole length is 2.3 cm. The mean blade length is 9 cm and the blade width is 5.5 cm.

Flowers

The bloom period is early midseason, the same bloom time as McIntosh (an unpatented variety) approximately May 9th at Cleveland, Minn. The color of the pedals when the bud is in full balloon stage is red-violet, N57B according to The R.H.S. Colour Chart. The pedicel is green (135B according to The R.H.S. Colour Chart) and measures 1.6 cm. The flower is single having typically 5 (five) petals and mean diameter of each petal is 1.7 cm in length and 1.3 cm wide. The petals are ovate in shape and overlapping one another when flower is fully open. The colors of the upper sides of the petals are white with light pink tinges (62D to 69D according to The R.H.S. Colour Chart). The lower sides of the petals are white tinged with light red-violet (62D with tinges of N66B according to The R.H.S. Colour Chart). The stamen commonly number 13 per flower and measure 0.5 cm in length. Pistils appear to divide into four per flower and rise approximately 0.4 cm.

Fruit

The variety is remarkable for its early season of ripening with the fruit characterized as marvelously crisp and juicy with a pleasant balance of sweet and tart flavor. The fruit has an exciting exterior color and pattern, crisp and juicy texture and a startling interior color with a burst of flavor unanimously described as very good to excellent. The flesh is very white (155B according to The R.H.S. Colour Chart). The fruits are flat-globose (slightly oblate) in shape with a mean measurement of 8.2 cm by 6.5 cm. They are asymmetric in shape and absent of ribbing. They are absent of crowning at the distal end. The aperture of the eye is half open and the size of the eye is medium. The calyx is persistent in mature fruit and sepals are medium in length and touching at the base. The calyx basin is medium 6 cm in depth. The width of the eye basin is 2.5 cm depth of stalk cavity is 2.2 cm and the width of the stalk cavity is 3 cm. The stalk is medium in width 0.2 cm and short in length 2 cm.

The surface of the fruit is smooth and has light bloom. The skin is absent of waxiness and is medium in thickness. Translucency of the skin is not noticeable. The background color of the skin is yellow (157C to 155B according to The R.H.S. Colour Chart). Overall 60% to 90% of the overcolor of the skin is red-orange (42A according to The R.H.S. Colour Chart) stripe banded depending on exposure to the sun as well as degree of maturity. The stalk basin remains green (152C to 152A to 141 C according to The R.H.S. Colour Chart) in color until after approximately seven weeks in cold storage. During the storage period, the red orange (42A according to The R.H.S. Colour Chart) overcolor progresses to become increasingly over the entire apple and the green (152C to 152A to 141 C according to The R.H.S. Colour Chart) of the stalk basin becomes smaller. The white (157C to 155B according to The R.H.S. Colour Chart) starburst markings on the skin appear early on as the overcolor develops when the fruit is nearing maturity on the tree. Lenticels are very white (156D according to The R.H.S. Colour Chart). These markings are very prominent and vary in size and placement but are most obvious where the red-orange (42A according to The R.H.S. Colour Chart) over color is more brilliantly developed.

The flesh of the fruit is startlingly white (155B according to The R.H.S. Colour Chart). It does not oxidize or turn brown for a day or longer after slicing. Russeting is absent. In a median cross section through the locules, the core line is absent or very weak. The locules are closed. The seed is brown (166A according to The R.H.S. Colour Chart) in color and normal in shape.

The size, fruit flesh pressure, amount of juice produced, brix, and juice pH were determined for freshly picked apples from the first picking in late August. An apple sized 7 cm weighed 95 g. An apple sized 7.6 cm weighed 149 g. The juice was extracted from the two apples and yielded 100 mL. The brix was measured at 14, pH was 2.97, with acid content at 1.1 g per 100 mL as tartaric acid. On apples from this picking the pentrometer test topped at 18–20 psi. A riper apple from the picking topped at 16 psi.

In another test, from a picking done 1 week later, the pentrometer test average as 18 psi. This second picking yielded apples of 7.6 cm weighing 142.4 g, of 8 cm weighing 165 g, of 7.5 cm weighing 124 g. The brix was 14.5, pH was 2.95, and acid as 1.23 g per 100 mL as tartaric acid. Three apples from this picking yielded 225 mL of juice.

Fruiting

The trees of the Stella Minnesota bear annually. Productivity is moderate and has been consistently productive every year from 1997 through 2002. The fruit matures in late August at Cleveland Minn. at the same time as Paulared and usually a week ahead of McIntosh (unpatented cultivar). The fruits hang consistently (do not drop prematurely) and usually can be harvested in two pickings. The storage life in cold storage without atmospheric modification is longer compared to other varieties that mature in nearly the same date. The optimal period of use would be within six to seven weeks after harvest, but the Stella Minnesota apple does not undergo objectionable changes in storage such as the sudden change in flesh texture and starch/sugar balances that are notable in Paulared, Liberty and State Fair apple varieties.

I claim:

1. A new and distinct variety of apple tree substantially as shown and described herein and combining the characteristics of having a compact form with vigorous growth, angled branches and annual fruit production, the fruit ripening early in the season yet having a long storage life, non-browning characteristics, star-like features in the skin, excellent flavor, crisp, juicy texture, and a utility in common apple products.

* * * * *